United States Patent
Brennan et al.

(10) Patent No.: US 9,625,739 B2
(45) Date of Patent: Apr. 18, 2017

(54) PUPIL SIZE-INDEPENDENT LENS DESIGN AND METHOD FOR PREVENTING AND/OR SLOWING MYOPIA PROGRESSION

(71) Applicant: Johnson & Johnson Vision Care, Inc., Jacksonville, FL (US)

(72) Inventors: Noel A. Brennan, Ponte Vedra Beach, FL (US); Khaled A. Chehab, Jacksonville, FL (US); Michael J. Collins, Queensland (AU); Xin Wei, Arlington, TX (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 28 days.

(21) Appl. No.: 14/464,097

(22) Filed: Aug. 20, 2014

(65) Prior Publication Data

US 2016/0054587 A1 Feb. 25, 2016

(51) Int. Cl.
  G02C 7/06 (2006.01)
  A61F 2/14 (2006.01)
  A61F 2/16 (2006.01)
  G02C 7/04 (2006.01)

(52) U.S. Cl.
  CPC .............. *G02C 7/06* (2013.01); *A61F 2/1451* (2015.04); *A61F 2/16* (2013.01); *G02C 7/041* (2013.01); *G02C 7/044* (2013.01); *G02C 2202/24* (2013.01)

(58) Field of Classification Search
  CPC ...... G02C 7/06; G02C 7/041; G02C 2202/24; G02C 7/044; A61F 2/1451; A61F 2/16
  USPC ..................................................... 351/159.05
  See application file for complete search history.

(56) References Cited

U.S. PATENT DOCUMENTS

| 6,045,578 A | 4/2000 | Collins et al. |
| 2009/0141235 A1* | 6/2009 | Collins et al. ............ 351/160 R |
| 2010/0066973 A1 | 3/2010 | Portney |
| 2010/0195044 A1 | 8/2010 | Collins |
| 2012/0062836 A1 | 3/2012 | Tse |

(Continued)

FOREIGN PATENT DOCUMENTS

| AU | 2013202694 | * 10/2013 | ............... A61F 9/00 |
| EP | 2762953 A1 | 8/2014 | |
| WO | WO2014059465 A1 | 4/2014 | |

OTHER PUBLICATIONS

Walraven et al. "Relation between Directional Sensitivity and Spectral Response Curves in Human Cone Vision," Journal of the Optical Society of America, vol. 50, No. 8, pp. 780-784, 1960.*

(Continued)

*Primary Examiner* — Jordan Schwartz
*Assistant Examiner* — George G King
(74) *Attorney, Agent, or Firm* — Carl J. Evens

(57) ABSTRACT

A lens includes a center of the ophthalmic lens having a negative power that provides foveal vision correction for myopia; a first peripheral zone surrounding the center having a power that gradually increases to a first peak having a dioptric power that is more positive than at the center; and a second peripheral zone surrounding the first peripheral zone and having a second peak having a dioptric power that is more positive than at the center and that is different than the power at the first peak. The power profile slows, retards, or prevents myopia progression independent of pupil size.

2 Claims, 6 Drawing Sheets

(56) References Cited

U.S. PATENT DOCUMENTS

2012/0320334 A1    12/2012  Ho
2013/0090730 A1     4/2013  Weeber

OTHER PUBLICATIONS

European Search Report for corresponding European Patent Appln. No. 15181626.1 dated Nov. 19, 2015.

* cited by examiner

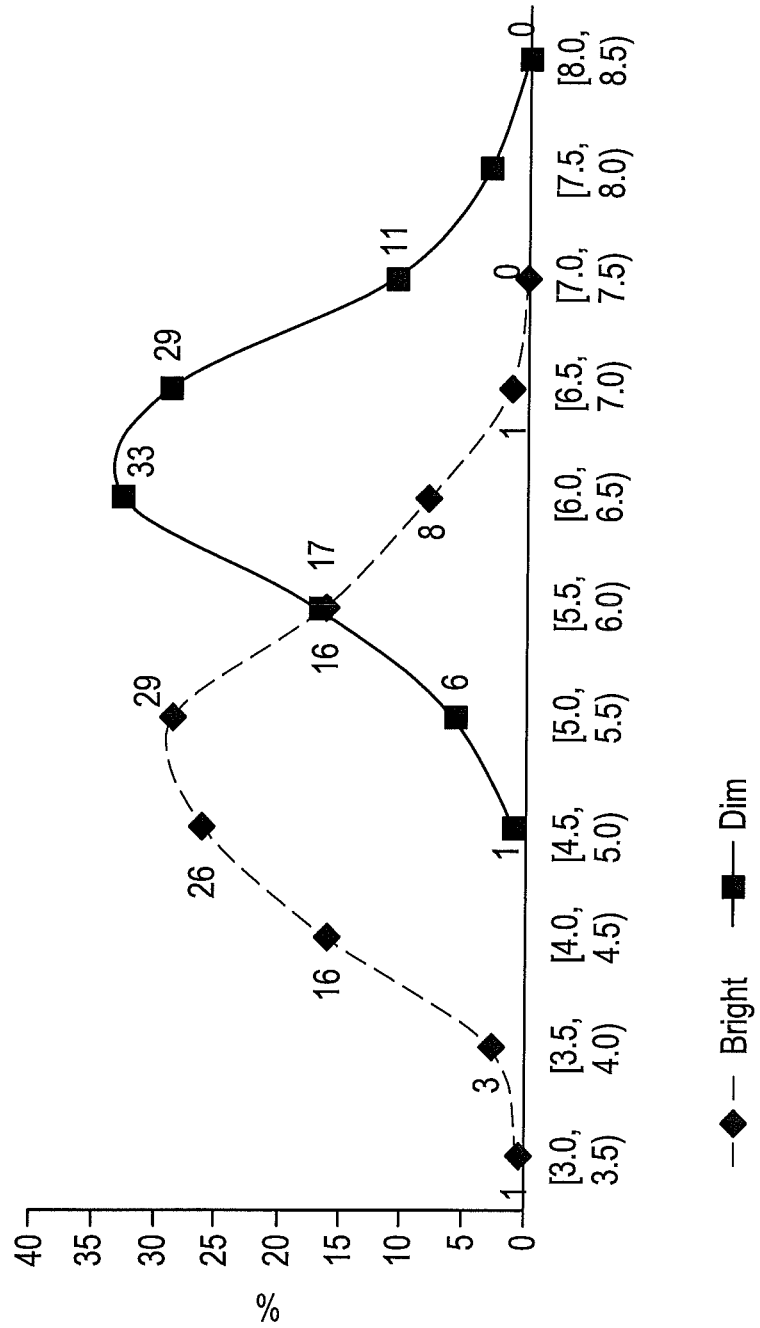

Power Profile

Relative Power Energy

Power Profile

Relative Power Energy

Power Profile

Relative Power Energy

PUPIL SIZE-INDEPENDENT LENS DESIGN AND METHOD FOR PREVENTING AND/OR SLOWING MYOPIA PROGRESSION

BACKGROUND OF THE INVENTION

Field of the Invention

The present invention relates to ophthalmic lenses, and more particularly, to contact lenses designed to slow, retard, or prevent myopia progression. The ophthalmic lenses of the present invention comprise power profiles having positive spherical aberration for both small and large entrance pupil sizes, for example pupil sizes having a diameter of 3.0 mm to 7.0 mm, which are suitable for the use in controlling or reducing the progression of myopia.

Discussion of the Related Art

Common conditions which lead to reduced visual acuity include myopia and hyperopia, for which corrective lenses in the form of spectacles, or rigid or soft contact lenses, are prescribed. The conditions are generally described as the imbalance between the length of the eye and the focus of the optical elements of the eye. Myopic eyes focus in front of the retinal plane and hyperopic eyes focus behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow long enough.

Myopia has a high prevalence rate in many regions of the world. Of greatest concern with this condition is its possible progression to high myopia, for example greater than five (5) or six (6) diopters, which dramatically affects one's ability to function without optical aids. High myopia is also associated with an increased risk of retinal disease, cataracts, and glaucoma.

Corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition, but is merely prosthetic or intended to address symptoms.

Most eyes do not have simple myopia or hyperopia, but have myopic astigmatism or hyperopic astigmatism. Astigmatic errors of focus cause the image of a point source of light to form as two mutually perpendicular lines at different focal distances. In the following discussion, the terms myopia and hyperopia are used to include simple myopia or myopic astigmatism and hyperopia and hyperopic astigmatism respectively.

Emmetropia describes the state of clear vision where an object at infinity is in relatively sharp focus with the crystalline lens relaxed. In normal or emmetropic adult eyes, light from both distant and close objects and passing though the central or paraxial region of the aperture or pupil is focused by the crystalline lens inside the eye close to the retinal plane where the inverted image is sensed. It is observed, however, that most normal eyes exhibit a positive longitudinal spherical aberration, generally in the region of about +0.50 Diopters (D) for a 5.0 mm aperture, meaning that rays passing through the aperture or pupil at its periphery are focused +0.50 D in front of the retinal plane when the eye is focused to infinity. As used herein the measure D is the dioptric power, defined as the reciprocal of the focal distance of a lens or optical system, in meters.

The spherical aberration of the normal eye is not constant. For example, accommodation (the change in optical power of the eye derived primarily though changes to the crystalline lens) causes the spherical aberration to change from positive to negative.

U.S. Pat. No. 6,045,578 discloses that the addition of positive spherical aberration on the contact lens will reduce or control the progression of myopia. The method includes changing the spherical aberration of an ocular system to alter the growth in eye length. In other words, emmetropisation may be regulated by spherical aberration. In this process, the cornea of a myopic eye is fitted with a lens having increasing dioptric power away from the lens center. Paraxial light rays entering the central portion of the lens are focused on the retina of the eye, producing a clear image of an object. Marginal light rays entering the peripheral portion of the cornea are focused in a plane between the cornea and the retina, and produce positive spherical aberration of the image on the latter. This positive spherical aberration produces a physiological effect on the eye which tends to inhibit growth of the eye, thus mitigating the tendency for the myopic eye to grow longer.

Currently, the addition of the positive spherical aberration is defined in a manner that applies to only one specific pupil size. Since pupils, for example pediatric pupils, change dramatically with light level, there is a need to design optics that carries more consistent positive spherical aberration across various pupil sizes, for example, ranging from about 3 mm to about 7 mm in diameter, especially in the context of myopia control.

SUMMARY OF THE INVENTION

The pupil size-independent lens design of the present invention overcomes the limitations of the prior art by ensuring foveal distance vision correction and providing a power profile having a more consistent positive spherical aberration for both small and large pupil sizes thereby slowing, retarding, or preventing myopia progression.

In accordance with one aspect, the present invention is directed to an ophthalmic lens for at least one of slowing, retarding, or preventing myopia progression. An ophthalmic lens comprises a center of the ophthalmic lens having a negative power that provides foveal vision correction for myopia; a first peripheral zone surrounding the center and having a power that increases to a first peak having a dioptric power that is more positive than at the center; and a second peripheral zone surrounding the first peripheral zone and having a second peak having a dioptric power that is more positive than at the center and that is different than the dioptric power at the first peak. The lens has a power profile that slows, retards, or prevents myopia progression independent of pupil size.

In accordance with another aspect, the present invention is directed to a method for at least one of slowing, retarding or preventing myopia progression. A lens comprises a center of the ophthalmic lens having a negative power that provides foveal vision correction for myopia; a first peripheral zone surrounding the center having a power that increases to a first peak having a dioptric power that is more positive than at the center; and a second peripheral zone surrounding the first peripheral zone and having a second peak having a dioptric power that is more positive than at the center and that is different than the power at the first peak. Accordingly, the growth of the eye is altered independent of pupil size.

The contact lens of the present invention is designed with a pupil size-independent power profile. A lens comprises a power profile having a minimum relative power energy of 5, thereby providing a more consistent spherical aberration across pupil diameters between about 3 mm and about 7 mm.

The pupil size-independent lens contact lens design of the present invention provides a simple, cost-effective and efficacious means and method for preventing and/or slowing myopia progression which is increasing throughout the world at an increasing rate.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 2 is a graph showing the pupil sizes of children at bright and dim luminescence levels.

DETAILED DESCRIPTION OF THE INVENTION

Figure 1:
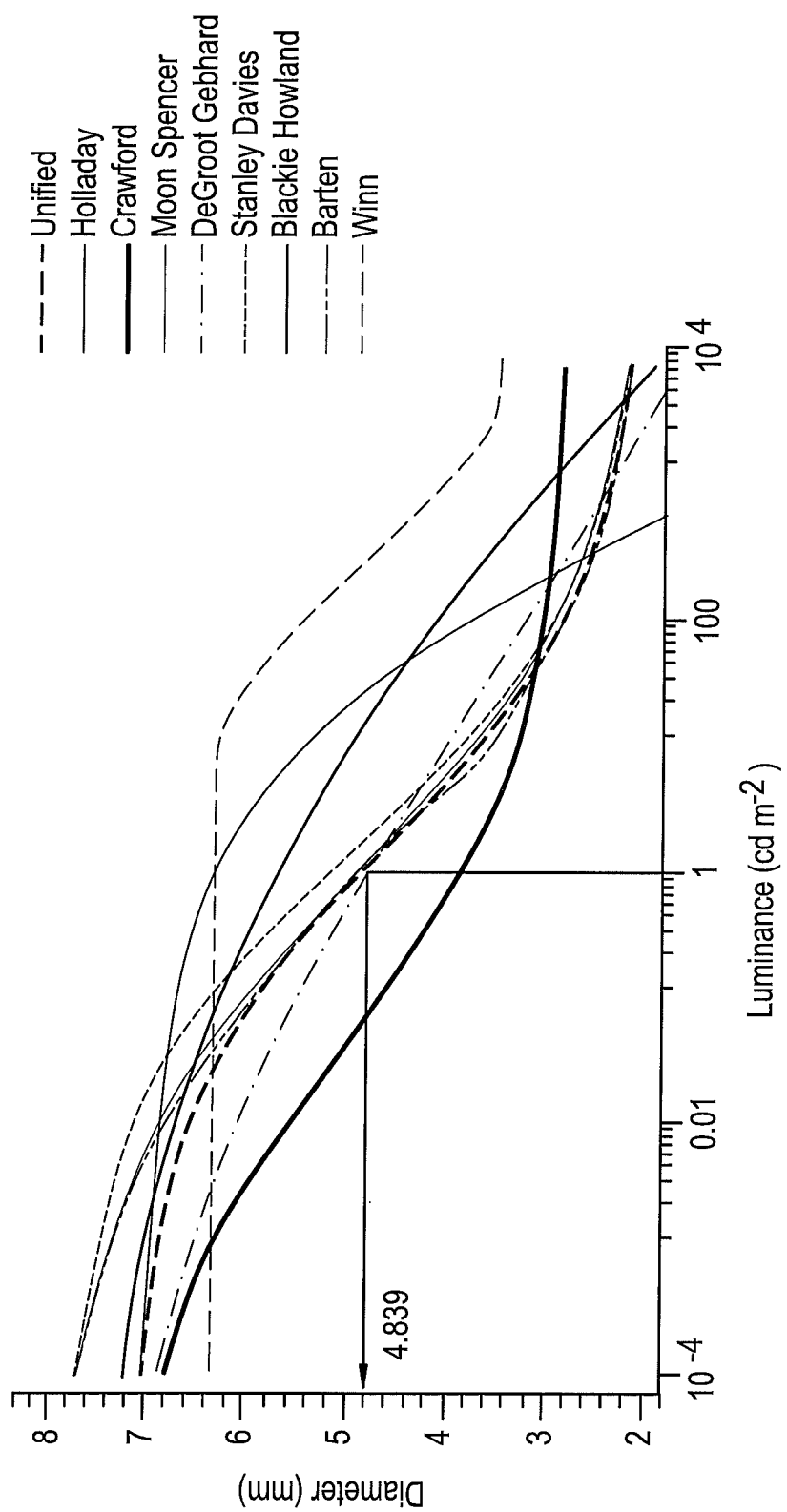
FIG. 1 is a graph of pupil diameter versus luminance.

Known power profiles for lenses may have a longitudinal positive spherical aberration based on the size of a pupil, but do not account for the different levels of light that enters the eye as the pupil size changes. As illustrated in FIG. 1, pupil size changes significantly, for example between 3.0 mm and 7.0 mm in diameter, as luminance changes.

With reference now to FIG. 2, a graph is shown that was obtained from a clinical study of 300 children (600 eyes) showing the percentage of pupils at bright and dim luminescence levels and the corresponding pupil sizes. As shown, pupil size can change dramatically with light level.

According to the present invention, Relative Power Energy (RPE) is used to develop lens power profiles having more consistent positive spherical aberration at both small and large pupil sizes, for example for pupil sizes ranging from 3.0 mm to 7.0 mm, thereby providing better treatment or prevention of myopia progression than known lenses. Relative Power Energy (RPE) may be calculated as follows.

First, the power energy in a first region of the pupil is calculated according to formula (1) (e.g., depending on the pupil size this may correspond to about 15.52 percent of the pupil area):

$$PE_C = \int_0^{30\% \; d/2} 2\pi s(r) f(r) dr. \tag{1}$$

Second, the power energy in a second region of the pupil surrounding the first region is calculated according to formula (2) (e.g., depending on the pupil size this may correspond to about 84.48 percent of the pupil area):

$$PE_A = \int_{30\% \; d/2}^{d/2} 2\pi s(r) f(r) dr. \tag{2}$$

Finally, the Relative Power Energy (RPE) is calculated according to formula (3):

$$RPE(d) = PE_c(d) - PE_A(d), \tag{3}$$

wherein r is a radial position;
d is the diameter of a pupil (entrance pupil size);
f(r) represents a dioptric power (D) of the lens; and
s(r) represents the Stiles-Crawford effect.

Figure 3A:
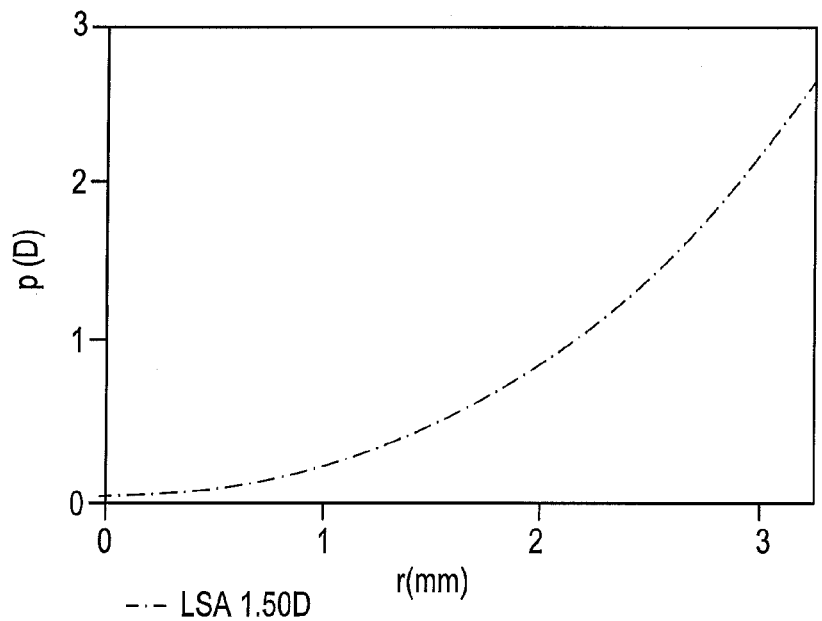
FIG. 3A is an illustration of a power profile for a lens having a positive longitudinal spherical aberration of +1.50 D.
Figure 3B:
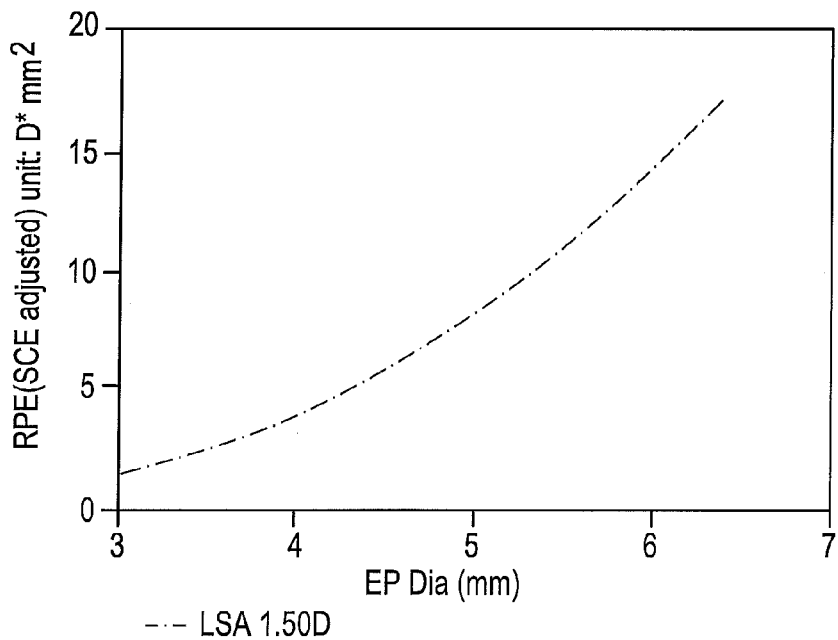
FIG. 3B is a graph of the Relative Power Energy for the lens of FIG. 3A.

With reference now to FIG. 3A, the power profile of a lens having +1.50 D longitudinal positive spherical aberration at 2.5 mm radial position (an example from U.S. Pat. No. 6,045,578) is illustrated. The RPE for this lens is calculated for different entrance pupil (EP) sizes. The RPE curve is plotted in FIG. 3B. The RPE value increases as the pupil size increases as shown in the graph of FIG. 3B.

It can be observed that the RPE is low for small entrance pupil sizes (i.e., less than 5 for EP sizes of between 3.0 and 4.0 mm). In fact, the RPE value as measured at a 6.5 mm entrance pupil (EP) is about 8 times more than the value of a 3.0 mm entrance pupil. Accordingly, the lens of FIG. 3A does not have a consistent spherical aberration across various pupil sizes. Therefore, although this lens design may retard the rate of myopia progression for large pupils, it may have little effect in preventing or controlling myopia progression for small pupils.

Figure 4A:
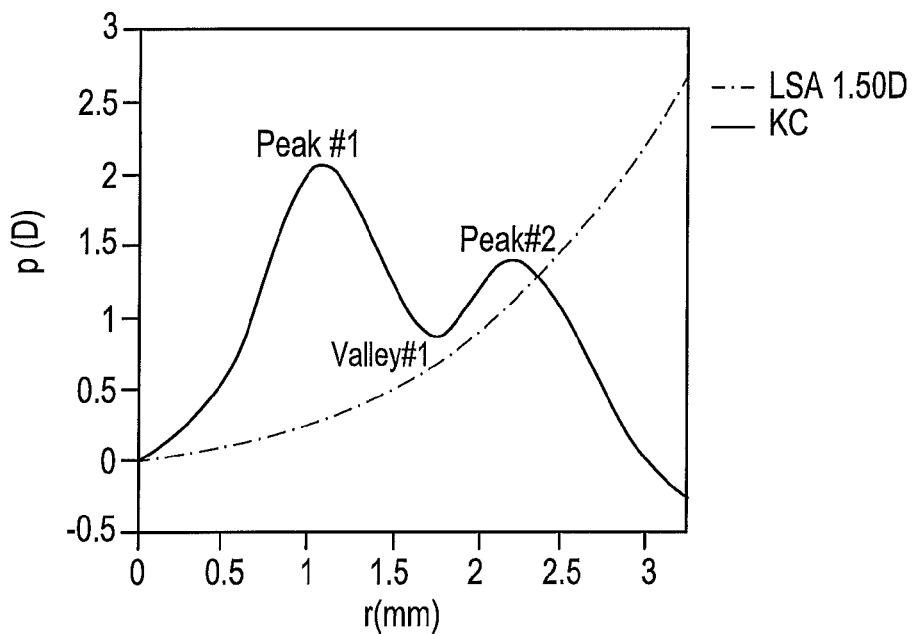
FIG. 4A is an illustration of a power profile of a first pupil size-independent lens according to the present invention.

With reference now to FIG. 4A, a power profile (KC) of a first pupil size-independent lens according to the present invention is shown and contrasted with the power profile of FIG. 3A. The power at the geometric center of the lens may have a negative focal power that matches an existing myopic distance vision condition, thereby providing foveal vision correction. The lens comprises a first peripheral zone where the refractive power rises gradually and continuously to a first peak (Peak #1). In specific embodiments, a location of the first peak may be at least 0.75 mm and at most 2.0 mm away from the center of the lens, for example at about 1.09 mm as shown. In specific embodiments, a magnitude of the positive power at the first peak may range between +1.00 D and +15.00 D with respect to the power at the center of the lens, for example about +2.05 diopters as shown.

The power profile (KC) also comprises a second peripheral zone where the refractive power drops from the first peak to a valley (Valley #1) and then increases from the valley to a second peak (Peak #2). In specific embodiments, a location of the second peak may be at least 2.00 mm and at most 3.50 mm away from the center of the lens, for example about 2.20 mm away from the center. In specific embodiments, a magnitude of the positive power at the second peak with respect to the power at the center of the lens may range between +1.00 D and +15.00 D, for example +1.40 diopters as shown. In specific embodiments, the magnitude of positive power at second peak is equal to or less than that at the first peak.

In FIG. 4A, the location of the valley is about 1.75 mm from the center of the lens. The magnitude of the positive power of the valley with respect to that at the center of the lens is +0.85 diopters. In specific embodiments, this magnitude may be at least 0.50 diopters smaller than the magnitude of the first peak or the second peak. The lens design also comprises a third region where the positive power continuously drops from the second peak to a margin of the optical zone of the lens.

Figure 4B:
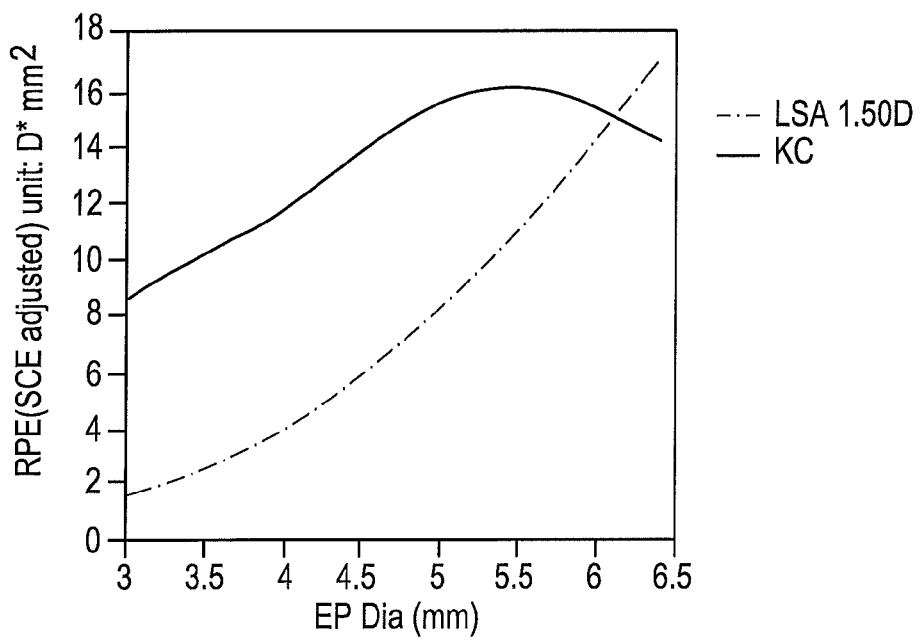
FIG. 4B is a graph of the Relative Power Energy for the lens of FIG. 4A.

With reference now to FIG. 4B, the RPE of the lens design of FIG. 4A is shown in comparison to the RPE of the lens of FIG. 3A. The pupil-size independent lens according to the present invention has a flatter RPE curve. The RPE is 5 or more, for example 8 or more, for pupil sizes ranging from 3.0 mm to about 6.5 mm. In contrast, the RPE of the lens of FIG. 3A has a smaller RPE at a pupil size less than 6.0 mm and dramatically less for pupil sizes of less than 5.5 mm. Accordingly, the lens design of FIG. 4A has a more consistent positive spherical aberration across a greater range of pupil sizes, especially smaller pupil sizes. The lens design of FIG. 4A effectively prevents, slows, or retards the rate of myopia progression, not only for large pupils, but also for small pupils.

Figure 5A:
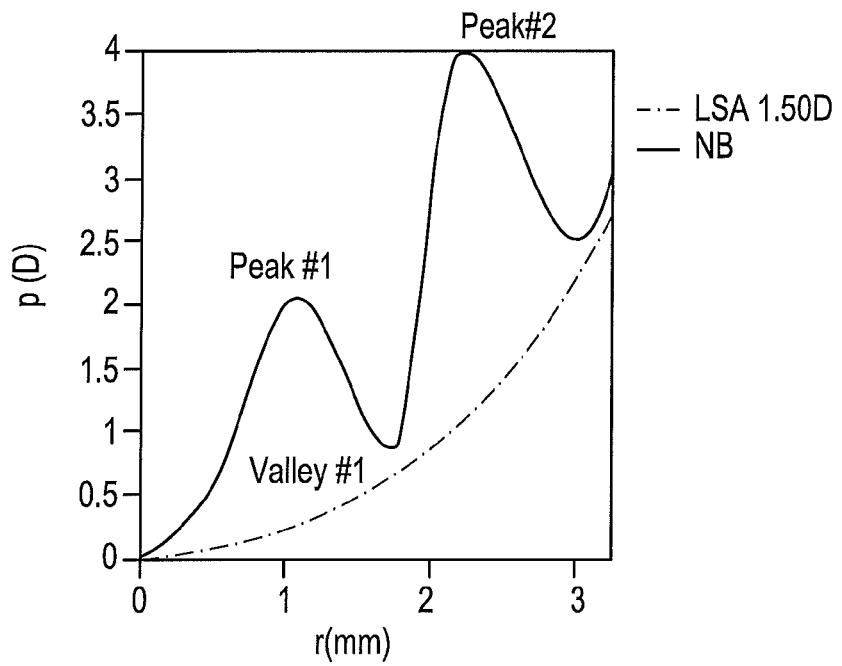
FIG. 5A is an illustration of a power profile of a second pupil size-independent lens according to the present invention.

With reference now to FIG. 5A, a power profile (NB) of a second pupil size-independent lens according to the present invention is shown and contrasted with the power profile of FIG. 3A. In FIG. 5A, the location and magnitude of the positive power at the first peak and the valley are similar to those of the first pupil-size independent lens of FIG. 4A.

The location of second peak is also similar to that of the second peak in FIG. 4A. The positive power at second peak with respect to that at the center of the lens may range between +1.00 D and +15.00 D, for example about +4 D as shown, but is larger (e.g., twice as large as the +2.05 D of FIG. 4A) than the magnitude of the positive power at the first peak.

Figure 5B:
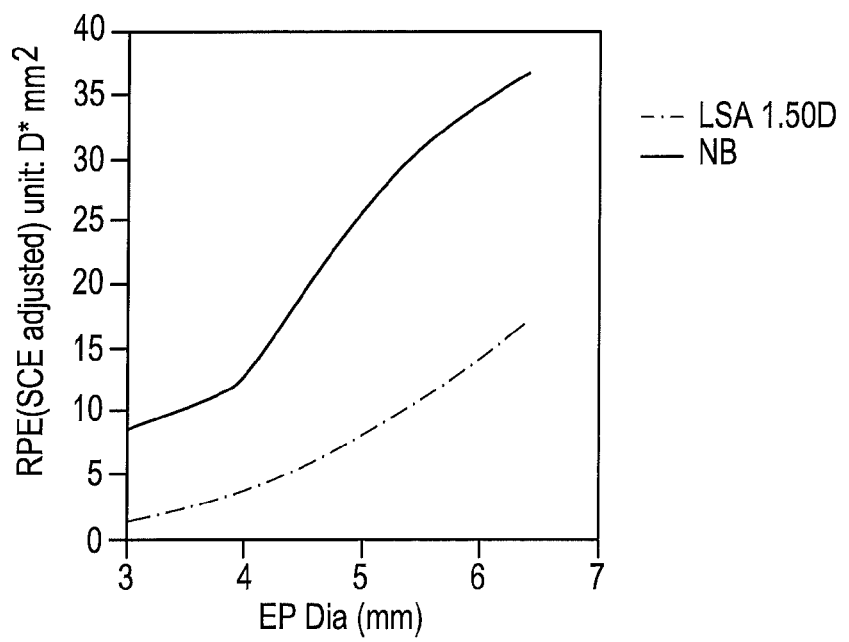
FIG. 5B is a graph of the Relative Power Energy for the lens of FIG. 5A.

With reference now to FIG. 5B, the second pupil-size independent lens design yields higher RPE values for small pupils compared to the lens design of FIG. 3A. Moreover, because the magnitude of the positive power of the second peak is higher than that of first peak, the RPE values of the second lens design become even larger than the first pupil-size independent design for larger pupils. The second lens design (NB) has a treatment efficacy in retarding myopia progression for small pupils and for larger pupil sizes.

According to the present invention, the power profile may be on a front surface or a back surface of a lens. In specific embodiments, power profile may be on a front surface of the lens to ensure a consistent profile when considering the effect of wrapping once a lens is placed on an eye.

Figure 6:
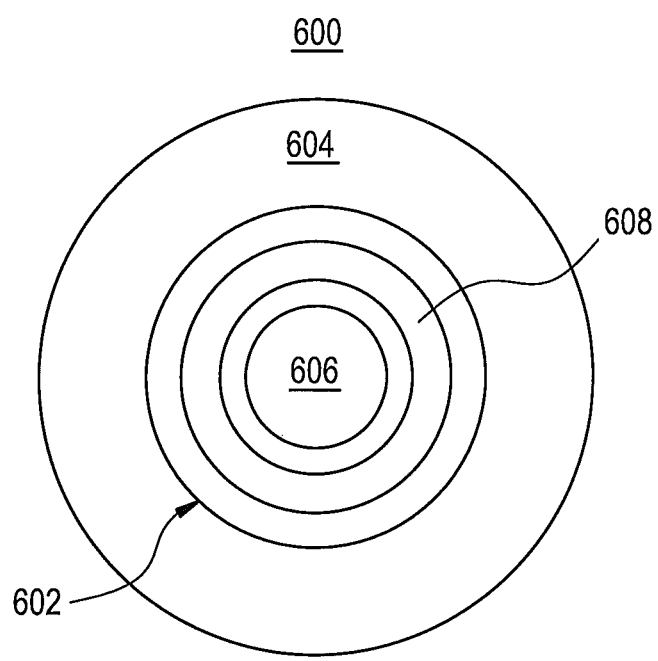
FIG. 6 is a diagrammatic representation of an exemplary contact lens in accordance with the present invention.

Referring to FIG. 6, there is illustrated a diagrammatic view of a contact lens 600 in accordance with an embodiment of the present invention. The contact lens 600 comprises an optic zone 602 and an outer zone 604. The optic zone 602 comprises a central zone 606 and at least one peripheral zone 608. In specific embodiments, the diameter of the optic zone 602 may be selected to be 8.0 mm, the diameter of the substantially circular zone 606 may be selected to be 4.0 mm, and the boundary diameters of an annular outer peripheral zone 608 may be 5.0 mm and 6.5 mm as measured from the geometric center of the lens 600. It is important to note that FIG. 6 only illustrates an exemplary embodiment of the present invention. For example, in this exemplary embodiment, the outer boundary of the at least one peripheral zone 608 does not necessarily coincide with the outer margin of the optic zone 602, whereas in other exemplary embodiments, they may coincide. The outer zone 604 surrounds the optic zone 602 and provides standard contact lens features, including lens positioning and centration. In accordance with one exemplary embodiment, the outer zone 604 may include one or more stabilization mechanisms to reduce lens rotation when on eye.

It is important to note that the various zones in FIG. 6 are illustrated as concentric circles, the zones may comprise any suitable round or non-round shapes such as an elliptical shape.

It is important to note that as the entrance pupil size of the eye varies among subpopulations. In certain exemplary embodiments, the lens design may be customized to achieve both good foveal vision correction and myopic treatment efficacy based on the patient's average pupil size. Moreover, as pupil size correlates with refraction and age for pediatric patients, in certain exemplary embodiments, the lens may be further optimized towards subgroups of the pediatric subpopulation with specific age and/or refraction based upon their pupil sizes. Essentially, the power profiles may be adjusted or tailored to pupil size to achieve an optimal balance between foveal vision correction and a more consistent special aberration across a range of pupil sizes.

Currently available contact lenses remain a cost effective means for vision correction. The thin plastic lenses fit over the cornea of the eye to correct vision defects, including myopia or nearsightedness, hyperopia or farsightedness, astigmatism, i.e. asphericity in the cornea, and presbyopia, i.e., the loss of the ability of the crystalline lens to accommodate. Contact lenses are available in a variety of forms and are made of a variety of materials to provide different functionality.

Daily wear soft contact lenses are typically made from soft polymer materials combined with water for oxygen permeability. Daily wear soft contact lenses may be daily disposable or extended wear disposable. Daily disposable contact lenses are usually worn for a single day and then thrown away, while extended wear disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from siloxane-containing polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

It is important to note that the pupil size-independent lens design of the present invention may be incorporated into any number of different contact lenses formed from any number of materials. Specifically, the pupil size-independent lens design of the present invention may be utilized in any of the contact lenses described herein, including, daily wear soft contact lenses, rigid gas permeable contact lenses, bifocal contact lenses, toric contact lenses and hybrid contact lenses. In addition, although the invention is described with respect to contact lenses, it is important to note that the concept of the present invention may be utilized in spectacle lenses, intraocular lenses, corneal inlays and onlays.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens for at least one of slowing, retarding or preventing myopia progression, the ophthalmic lens comprising:
   a center optic zone including optics to correct a myopic refractive error;
   a power profile with a first peripheral zone surrounding the center optic zone and having a power that increases from a power in the center optic zone to a first peak power of about +2 diopters above the power in the center optic zone at a radial distance of 1 mm from a geometric center of the center optic zone and then decreases to a first valley power of about +0.75 diopters at a radius of about 1.75 mm from the geometric center of the center optic zone; and
   a second peripheral zone surrounding the first peripheral zone and having a power that increases from the first valley power to a second peak power of about 1.25 diopters above the power in the center optic zone at a radius of about 2.25 mm and then decreases monotonically to an edge of the optic zone.

2. An ophthalmic lens for at least one of slowing, retarding or preventing myopia progression, the ophthalmic lens comprising:
   a center optic zone including optics to correct a myopic refractive error;
   a power profile with a first peripheral zone surrounding the center optic zone and having a power that increases from a power in the center optic zone to a first peak power of about +2 diopters above the power in the center optic zone at a radial distance of 1 mm from a geometric center of the center optic zone and then decreases to a first valley power of about +0.75 diopters at a radius of about 1.75 mm from the geometric center of the center optic zone; and
   a second peripheral zone surrounding the first peripheral zone and having a power that increases from the first valley power to a second peak power of about +4 diopters above the power in the center optic zone at a radius of about 2.25 mm and then decreases to a second valley power of about +2.5 diopters at a radius of about 3 mm from the geometric center of the center optic zone and then increase monotonically to an edge of the optic zone.

\* \* \* \* \*